(12) United States Patent
Fujikawa et al.

(10) Patent No.: US 8,809,246 B2
(45) Date of Patent: *Aug. 19, 2014

(54) BRAIDED HAIR WASHING METHOD

(75) Inventors: Susumu Fujikawa, Tokyo (JP); Kazuo Miyazaki, Kanagawa (JP)

(73) Assignees: Thales Inc., Tokyo (JP); TOWA Enzyme Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/943,751

(22) Filed: Nov. 10, 2010

(65) Prior Publication Data

US 2011/0112000 A1 May 12, 2011

(30) Foreign Application Priority Data

Nov. 12, 2009 (JP) ................................ 2009-258797

(51) Int. Cl.
- *A61Q 5/02* (2006.01)
- *A61Q 19/10* (2006.01)
- *A61K 8/19* (2006.01)
- *A61K 8/20* (2006.01)
- *C11D 7/10* (2006.01)
- *C11D 7/12* (2006.01)
- *C11D 7/42* (2006.01)

(52) U.S. Cl.
USPC ........... 510/119; 510/393; 510/420; 510/435; 424/70.1; 514/20.7; 132/202; 134/42

(58) Field of Classification Search
USPC ......... 510/119, 135, 393, 420, 435; 424/70.1; 514/20.7; 132/202; 134/42
See application file for complete search history.

(56) References Cited

U.S. PATENT DOCUMENTS

| | | | |
|---|---|---|---|
| 2,691,636 A | 10/1954 | Stayner | |
| 4,556,554 A | 12/1985 | Calvo | |
| 5,053,222 A | 10/1991 | Takasu et al. | |
| 5,078,898 A | 1/1992 | Jars | |
| 5,160,655 A | 11/1992 | Donker et al. | |
| 5,347,665 A | 9/1994 | Kumon et al. | |
| 5,448,966 A | 9/1995 | McKinnon et al. | |
| 5,454,982 A | 10/1995 | Murch et al. | |
| 5,656,264 A | 8/1997 | Hanada et al. | |
| 5,657,719 A | 8/1997 | Whan | |
| 5,766,579 A * | 6/1998 | Earles | 424/70.1 |
| 5,769,029 A | 6/1998 | Marshall | |
| 5,904,735 A | 5/1999 | Gutierrez et al. | |
| 6,106,828 A | 8/2000 | Bisgard-Frantzen et al. | |
| 6,121,215 A | 9/2000 | Rau | |
| 6,248,338 B1 | 6/2001 | Muller et al. | |
| 6,416,756 B1 | 7/2002 | Olsen et al. | |
| 6,662,600 B1 | 12/2003 | Field et al. | |
| 7,635,671 B2 * | 12/2009 | Miyazaki et al. | 510/320 |
| 7,854,234 B2 * | 12/2010 | Maillefer et al. | 132/202 |
| 8,216,557 B2 | 7/2012 | Miyazaki et al. | |
| 2002/0077265 A1 | 6/2002 | Buzzacarini et al. | |
| 2002/0128165 A1 | 9/2002 | Baker et al. | |
| 2002/0137654 A1 | 9/2002 | Hage et al. | |
| 2004/0022751 A1 * | 2/2004 | Maillefer et al. | 424/70.2 |
| 2004/0151684 A1 | 8/2004 | Mori et al. | |
| 2005/0026269 A1 | 2/2005 | Kottwitz et al. | |
| 2005/0026299 A1 | 2/2005 | Bhattacharjee et al. | |
| 2007/0191261 A1 * | 8/2007 | Davis | 514/2 |
| 2008/0083440 A1 | 4/2008 | Miyazaki et al. | |
| 2009/0117067 A1 * | 5/2009 | Baltimore | 424/70.6 |
| 2009/0214512 A1 * | 8/2009 | Miyazaki et al. | 424/94.63 |

FOREIGN PATENT DOCUMENTS

| | | |
|---|---|---|
| EP | 0376705 A1 | 7/1990 |
| EP | 0839905 A1 | 5/1998 |
| EP | 1 913 931 A1 | 4/2008 |
| JP | 60-89413 A | 5/1985 |
| JP | 62-238214 A | 10/1987 |
| JP | 63-130514 A | 6/1988 |
| JP | 2-69600 A | 3/1990 |
| JP | 2-227500 A | 9/1990 |
| JP | 5-320028 A | 12/1993 |
| JP | 7-233037 A | 9/1995 |
| JP | 8-176005 A | 7/1996 |
| JP | 9-157138 A | 6/1997 |
| JP | 2000-95651 A | 4/2000 |
| JP | 2003-126665 A | 5/2003 |
| JP | 2003-210240 A | 7/2003 |
| JP | 2004-534528 A | 11/2004 |
| JP | 2005-177119 A | 7/2005 |
| JP | 2006-34473 A | 2/2006 |
| JP | 2006-68631 A | 3/2006 |
| JP | 2007-31376 A | 2/2007 |
| JP | 2007-130601 A | 5/2007 |
| JP | 2007-252434 A | 10/2007 |
| JP | 2008-94726 A | 4/2008 |

OTHER PUBLICATIONS

Extended European Search Report, dated May 19, 2011, for European Application No. 10191008.1.

(Continued)

*Primary Examiner* — Lorna M Douyon

(74) *Attorney, Agent, or Firm* — Birch, Stewart, Kolasch & Birch, LLP

(57) ABSTRACT

A braided hair washing method includes washing braided hair using a washing agent that includes a microbubble washing composition and microbubbles, the microbubble washing composition including a protease and a lipase. The braided hair washing method can conveniently and effectively wash braided hair without collapsing the hairstyle.

6 Claims, 3 Drawing Sheets

(56) References Cited

OTHER PUBLICATIONS

Smoore et al., "Making Locks; Keepings Locks Clean", The Dread FAQ, http://www.geocities.com/dreadfaq/index.html , Mar. 2002, XP002263624.
Examiner Interview Summary Record for U.S. Appl. No. 11/826,989 dated Oct. 8, 2008.
Health Beauty, WebMd, http://www.webmd.com/healthy-beauty/sensitive-skin-20-questions (retrieved online Sep. 8, 2011), 4 pages provided.
International Search Report for Application No. PCT/JP2009/059187 dated Aug. 25, 2009.
Keshohin Handbook, Nikko Chemicals Co., Ltd., Nov. 1, 1996, pp. 471-473, 485 (with English translation).
Melanoma Treatment, Mayo Clinic, http://www.mayoclinic.org/melanoma/treatment.html (retrieved online Sep. 7, 2011), 3 pages provided.
Skin Disorders, http://www.skin-disorders.net (retrieved online Sep. 7, 2011), 4 pages provided.
Suwa Precision, "Micro Bubbles and its Applications", Mar. 23, 2006 (retrieved online Feb. 18, 2008), 1 page provided, XP002469734.
United States Notice of Allowance for U.S. Appl. No. 11/826,989 dated Aug. 10, 2009.
United States Notice of Allowance for U.S. Appl. No. 12/435,252 dated Feb. 9, 2012.
United States Notice of Allowance for U.S. Appl. No. 12/435,252 dated Jun. 19, 2012.
United States Office Action for U.S. Appl. No. 11/826,989 dated Jan. 18, 2008.
United States Office Action for U.S. Appl. No. 11/826,989 dated Mar. 20, 2009.
United States Office Action for U.S. Appl. No. 11/826,989 dated Nov. 26, 2008.
United States Office Action for U.S. Appl. No. 12/435,252 dated Jul. 21, 2011.
United States Office Action for U.S. Appl. No. 12/435,252 dated Sep. 15, 2011.
United States Office Action for U.S. Appl. No. 12/993,306 dated May 21, 2012.

* cited by examiner

BRAIDED HAIR WASHING METHOD

TECHNICAL FIELD

The present invention relates to a method of conveniently and effectively washing braided hair without collapsing the hairstyle.

BACKGROUND ART

In recent years, many people prefer a hairstyle formed by braiding hair (particularly dreadlocks) along with diversification of fashion.

Dreadlocks can be classified into many types, and formed by various methods. A skilled hairdresser normally forms dreadlocks by braiding hair by hand work. It takes time to complete dreadlocks. For example, the hair is braided, and the surrounding hair is wound around the braided hair. The hair is bundled by melting the surface of the hair on a fire, and formed into a cylindrical shape by further braiding and twisting the hair. These operations are performed one by one by hand work.

Therefore, people who wear dreadlocks desire to maintain their hairstyle without collapsing as long as possible. However, dreadlocks cannot be washed by a normal method. In particular, odors, dandruff, and an itch may occur in the summertime if washing is insufficient. This makes it difficult to maintain dreadlocks for a long time. On the other hand, the hairstyle may be collapsed if it is washed forcibly.

Patent Document 1 discloses a hair washing apparatus that includes a storage tank, a gas-dissolved water production means, and a microbubble generator including a bubble-generating nozzle. Patent Document 2 discloses a hair washing method that utilizes a hair washing apparatus that includes a discharge section that discharges a washing agent into a washing cap that covers a head, and a recovery section that recovers the washing agent discharged from the washing cap, wherein the washing agent recovered by the recovery section is discharged from the discharge section, mixed with microbubbles, and circulated. Patent Document 3 discloses a microbubble washing method that washes a human body or an animal using a washing agent that includes a microbubble washing composition containing a protease and a lipase, and microbubbles.

RELATED-ART DOCUMENT

Patent Document

Patent Document 1: JP-A-2005-327849
Patent Document 2: JP-A-2007-252434
Patent Document 3: JP-A-2008-94726

DISCLOSURE OF THE INVENTION

Problems to be Solved by the Invention

The present invention was conceived in view of the above situation. An object of the present invention is to provide a method of conveniently and effectively washing braided hair without collapsing the hairstyle.

Means for Solving the Problems

In order to achieve the above object, the inventors attempted to wash braided hair by the method disclosed in Patent Document 2, and found that the hair and the surface of the skin can be effectively cleaned, and odors, dandruff, and an itch can be removed without collapsing the hairstyle. This finding has led to the completion of the present invention.

Specifically, the present invention provides the following braided hair washing method (see (1) to (5)).

(1) A braided hair washing method comprising washing braided hair using a washing agent that includes a microbubble washing composition and microbubbles, the microbubble washing composition including a protease and a lipase.

(2) The method according to (1), wherein the microbubble washing composition includes the protease in an amount of 0.01 to 0.5 wt % based on the total amount of the microbubble washing composition, and includes the lipase in an amount of 0.1 to 1.0 wt % based on the total amount of the microbubble washing composition.

(3) The method according to (1) or (2), wherein the microbubble washing composition does not include a surfactant.

(4) The method according to any one of (1) to (3), wherein the microbubble washing composition further includes at least one alkali metal salt selected from the group consisting of alkali metal carbonates, alkali metal hydrogen carbonates, alkali metal sulfates, alkali halides, and alkali metal salts of boron.

(5) The method according to (4), wherein the microbubble washing composition includes the alkali metal salt in an amount of 80 to 99.5 wt % based on the total amount of the microbubble washing composition.

EFFECTS OF THE INVENTION

According to the present invention, braided hair such as dreadlocks can be conveniently and effectively washed without collapsing the hairstyle. It is economical since a hairstyle which it took a long time to create can be maintained and kept clean for a long time.

DESCRIPTION OF EXEMPLARY EMBODIMENTS

Figure 1:
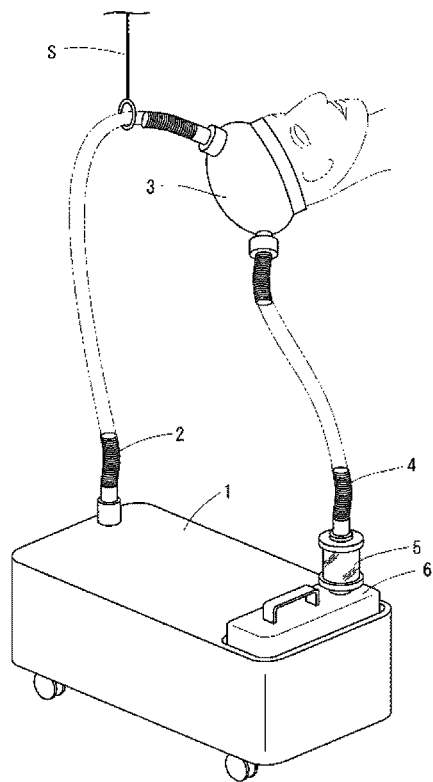
FIG. 1 is a view showing the configuration of a hair washing apparatus used in Example.

A braided hair washing method according to one embodiment of the present invention includes washing braided hair using a washing agent that includes a microbubble washing composition and microbubbles, the microbubble washing composition including a protease and a lipase.

The protease included in the microbubble washing composition according to one embodiment of the present invention (hereinafter may be referred to as "composition of the present invention") is an enzyme that catalyzes hydrolysis of a peptide bond.

The protease has a specific optimum pH, and is classified as an acidic proteinase, a neutral proteinase, or an alkaline proteinase. Any of these proteases may be used in the present invention without specific limitations.

Examples of the protease include, but are not limited to, chymotrypsin, subtilisin, pepsin, cathepsin D, thermolysin, papain, caspase, bromelain, actinidin, ficin, trypsin, pancreatin, and the like.

These proteases may be used either individually or in combination.

Specific examples of the protease include Protin AC10F (manufactured by Daiwa Kasei K.K.), Savinase, Alcalase, Esperase, Durazyme (manufactured by Novozymes), Maxapem, Maxatase (manufactured by Gist-brocades), Bioplaze (manufactured by Nagase Biochemicals, Ltd.), and the like.

It is preferable to use at least pancreatin in order to obtain excellent washing effects. It is more preferable to use pancreatin and another protease in combination.

The amount of protease used is not particularly limited. The protease is preferably used in an amount of 0.01 to 0.5 wt %, and more preferably 0.2 to 0.3 wt %, based on the total amount of the composition.

The lipase included in the composition of the present invention is an enzyme that hydrolyzes fats into glycerol and a fatty acid.

Examples of the lipase include, but are not limited to, a lipase derived from *Rhizopus arrhizus*, a lipase derived from *Aspergillus niger*, and a lipase derived from a mold such as *Rhizopus delemar*; a lipase derived from yeast such as *Candida cylindracea*; a lipase derived from a bacteria such as Pseudomonas; a lipase that is present in the digestive tract tissues of a ruminant during a lactation period, such as pregastric lipase or oral lipase; pig liver lipase; and the like.

These lipases may be used either individually or in combination. It is preferable to use two or more lipases in order to obtain more excellent washing effects.

Specific examples of the lipase include Sumizyme NLS (manufactured by Shin-Nihon Kagaku Kogyo, Co., Ltd.), Lipase M "Amano" 10, Lipase M "Amano" 10, Lipase G "Amano" 50, Lipase F-AP15, Lipase AY "Amano" 30G, Lipase R "Amano" G, Lipase T "Amano", Lipase MER "Amano" (manufactured by Amano Enzyme Inc.), Picantase R8000, Picantase A (manufactured by Robin), Toyozyme and LIP (manufactured by Toyobo Co., Ltd.), Lilipase A-10FG, Lilipase AF-5 (manufactured by Nagase ChemteX Corporation), Grindamyl EXEL639 (manufactured by Danisco Culter Japan), Clear-Lens Lipo, Liporaze, Lipex, Lipozyme, Resinase, Paratase, Greasex, Lipopan, Novozyme 435, Lecitase (manufactured by Novozymes), Lipase MY, Lipase OF, Lipase PL, Lipase QLM, Lipase AL, Phospholipase D (manufactured by Meito Sangyo Co., Ltd.), Enzylon AKG (manufactured by Rakuto Kasei Industrial Co., Ltd.), Phospholipase A1 (manufactured by Sankyo Lifetech Co., Ltd.), Lipomod 699L, Lysomax PF (manufactured by Genencor Kyowa Co., Ltd.), and the like.

The lipase is normally used in an amount of 0.1 to 1.0 wt %, and preferably 0.3 to 0.8 wt %, based on the total amount of the composition.

It is preferable that the composition of the present invention does not include a surfactant from the viewpoint of obtaining more excellent washing effects. When the composition does not include a surfactant, the composition does not irritate the eyes even if the composition gets in the eyes when washing hair, and can be safely used.

It is preferable that the composition of the present invention further include an alkaline metal salt in addition to the protease and the lipase.

The alkali metal salt improves the washing effects, softens water (warm water), and functions as a filler.

Examples of the alkali metal salt include, but are not limited to, alkali metal carbonates such as sodium carbonate and potassium carbonate; alkali metal hydrogen carbonates such as sodium hydrogen carbonate and potassium hydrogen carbonate; alkali metal sulfates such as sodium sulfate and potassium sulfate; alkali halides such as sodium chloride and potassium chloride; alkali metal salts of boron such as sodium tetraborate (borax) and sodium borate; alkali metal silicates such as sodium silicate; alkali metal sulfides such as sodium sulfide; alkali metal nitrates such as sodium nitrate; alkali metal phosphates such as sodium phosphate and sodium dihydrogen phosphate; thiosulfates of an alkali metal such as sodium thiosulfate; and the like.

These alkali metal salts may be used either individually or in combination.

It is preferable that the composition of the present invention include at least one alkali metal salt selected from the group consisting of alkali metal carbonates, alkali metal hydrogen carbonates, alkali metal sulfates, alkali halides, and alkali metal salts of boron. It is more preferable that the composition include at least one alkali metal salt selected from the group consisting of sodium hydrogen carbonate, sodium sulfate, and borax. It is particularly preferable that the composition include sodium hydrogen carbonate, sodium sulfate, and borax.

The alkali metal salt is normally used in an amount of 80 to 99.5 wt %, and preferably 95 to 99 wt %.

When the washing composition of the present invention includes sodium hydrogen carbonate, sodium sulfate, and borax, sodium hydrogen carbonate is preferably used in an amount of 10 to 35 wt %, and particularly preferably 20 to 30 wt %, based on the total amount of the composition, sodium sulfate is preferably used in an amount of 30 to 70 wt %, and particularly preferably 40 to 60 wt %, based on the total amount of the composition, and borax is preferably used in an amount of 10 to 35 wt %, and particularly preferably 20 to 30 wt %, based on the total amount of the composition.

It is preferable that the composition of the present invention further include a silica-based desiccant.

The desiccant stabilizes the potency of the protease and the lipase. Examples of the silica-based desiccant include Sylysia (porous fine silica powder) and the like.

The silica-based desiccant is normally used in an amount of 0.01 to 1 wt %, and preferably 0.1 to 0.2 wt %.

The composition of the present invention may optionally further include an additional component. Examples of the additional component include inorganic salts other than the above alkali metal salts, a perfume, a coloring agent, an antiseptic agent, an antibacterial agent, a tackiness agent, a therapeutic component, and other additives normally used for a washing agent.

Examples of inorganic salts other than the alkali metal salts include magnesium salts such as magnesium carbonate and magnesium sulfate; calcium salts such as calcium carbonate, calcium nitrate, calcium thiosulfate, and calcium hydrogen phosphate; alum; and the like. The amount of inorganic salts may be appropriately determined insofar as the effects of the microbubble washing composition of the present invention are not collapsed.

Examples of the perfume include essential oils such as abies oil, angelica oil, anisie oil, copaiba balsam, basil oil, bay oil, bergamot oil, birch oil, rosewood oil, cajabute oil, cassia oil, acacia oil, cedar wood oil, chamomile oil, cinnamon oil, cinnamon leaf oil, citronella oil, elemi oil, eucalyptus oil, geranium oil, white-cedar leaf oil, cypress oil, lavandin oil, lavender oil, lemon oil, mint oil, neroli oil, nutmeg oil, oakmoss oil, ocotea oil, patchouli oil, palmarosa oil, plai oil, rose oil, rosemary oil, sandalwood oil, vetiver oil, and ylang ylang oil; synthetic perfumes such as synthetic musk (e.g., limonene, terpinolene, p-cymene, 9-decenol, mugol, myrcenol, borneol, vetiverol, t-butylcyclohexanol, anisole, anethole, safrole, citral, citronellal, cinnamaldehyde, anise aldehyde, cyclamen aldehyde, citral, acetophenone, benzophenone, acetonaphthone, nerone, and nitromusk), geranyl acetate, bornyl acetate, phenylethyl acetate, myrcenyl acetate, methyl benzoate, methyl cinnamate, methyl anthranilate, synthetic oakmoss, and coumarin; and the like.

The perfume is normally used in an amount of 0 to 0.5 wt %, and preferably 0.1 to 0.3 wt %.

As the coloring agent, a dye, a natural pigment, an inorganic dye, and the like may be used.

Examples of the dye include Red No. 2, Red No. 3, Red No. 102, Red No. 104-1, Red No. 105-1, Red No. 106, Red No. 213, Red No. 227, Red No. 230-1, Yellow No. 4, Yellow No. 5, Yellow No. 201, Yellow No. 201-1, Yellow No. 203, Orange No. 205, Green No. 3, Green No. 201, Green No. 204, Blue No. 1, Blue No. 2, Blue No. 205, Violet No. 201, Brown No. 201, and the like.

Examples of the natural pigment include a chlorophyll, a gardenia, a flavonoid, a carotinoide, a quinone, and a riboflavin.

Examples of the inorganic dye include titanium dioxide, talc, kaolin, mica, magnesium silicate, silicic anhydride, calcium carbonate, magnesium carbonate, and the like.

These coloring agents may be used either individually or in combination. The coloring agent is normally used in an amount of 0 to 0.5 wt %, and preferably 0.1 to 0.2 wt %.

Examples of the antiseptic agent include sodium benzoate, methyl p-hydroxybenzoate, ethyl p-hydroxybenzoate, propyl p-hydroxybenzoate, butyl p-hydroxybenzoate, isobutyl p-hydroxybenzoate, benzyl alcohol, benzalkonium chloride, and the like.

Examples of the tackiness agent include hydroxyethylcellulose, hydroxypropylmethylcellulose, methylcellulose, xanthan gum, polyethylene glycol distearate, polyethylene glycol monostearate, and the like.

The composition of the present invention may be produced by an arbitrary method. For example, a mixture of the protease, the lipase, and other optional components is homogenously stirred (mixed) using a stirrer such as a Vert-o-Mix, a Nauta mixer, a universal mixer/stirrer, a ribbon mixer, a V-shaped mixer, or the like to prepare a powder.

The composition of the present invention can reliably remove sebum and old keratin adhering to the surface of the pores of the skin within a short time, and keep the skin clean for a long time.

Since the composition of the present invention does not damage hair due to low irritation properties, the composition can be safely used for a person having a sensitive skin, an elderly person having a weak skin, or a human suffering from skin diseases.

When producing the washing agent, the composition of the present invention is normally used in an amount of 1 to 10 g, and preferably 3 to 7 g, per 6 to 10 liters of water.

The microbubbles are minute bubbles having a diameter of 50 μm or less, and are reduced in size and disappear (break) in water, differing from normal bubbles. The microbubbles remove dirt due to impact waves that occur when the microbubbles break. The microbubbles carry negative ions, and disappear in water while bonding to dirt (positive ions) and floating, so that the dirt floats. When washing hair using a washing agent including the microbubbles, minute microbubbles reach the interior of the pores, and adsorb and remove wastes.

A washing agent including the microbubbles is normally produced using a microbubble generator described below. Since water has a high surface tension, it is impossible to produce bubbles having a diameter of 100 μm or less by normal bubbling.

The microbubble generator is not particularly limited insofar as microbubbles can be produced. A known microbubble generator may be used. Examples of the microbubble generator include a device that produces microbubbles in a venturi tube (tube with a narrow constriction) or a shower head including an orifice plate (doughnut plate with a center opening) (e.g., JP-A-2006-116518 and Japanese Patent Application No. 2006-77553); a device that produces microbubbles by injecting a liquid mixed with a gas into a main pipe disposed in a liquid, and causing the liquid to collide with a collision wall disposed downstream of the main pipe (e.g., JP-A-2005-334869); a device that produces microbubbles by injecting pressurized air into water through a mesh member or a porous plate with a minute pore size using a pressurized air supply source such as an air pump (e.g., JP-A-2006-68631); a device that produces microbubbles by producing a whirling water stream, and shearing air using the water stream (e.g., JP-A-2003-126665); and the like. Among these, the microbubble generator disclosed in Japanese Patent Application No. 2006-77553 is preferable.

The washing method of the present invention includes washing braided hair using a washing agent that includes the composition of the present invention and microbubbles.

Specifically, an appropriate amount of the composition of the present invention is added to clean water (or warm water) to prepare a washing agent, and microbubbles are introduced into the washing agent. Braided hair is washed using the resulting washing agent.

Examples of the braided hair washing method using the washing agent including the composition of the present invention and the microbubbles include (i) a method that includes placing a washing agent obtained by adding an appropriate amount of the composition to clean water (or warm water) in a container such as a tank, introducing the washing agent into a microbubble generator by an appropriate method, introducing microbubbles into the washing agent using the microbubble generator, and washing braided hair while discharging the washing agent including the microbubbles from a shower nozzle; (ii) a method that includes placing clean water (or warm water) in a washing bath, adding an appropriate amount of the composition of the present invention to the washing bath to prepare a washing agent, introducing water (or warm water) including microbubbles into the washing agent from a nozzle connected to a microbubble generator to prepare a washing agent including microbubbles, and washing braided hair using the resulting washing agent; and the like. These methods may be used in combination.

When using the method (i), it is preferable to circulate the washing agent while removing contaminants and the like using a filter in order to efficiently utilize the washing agent.

For example, braided hair is washed as follows using an apparatus shown in FIG. 1.

In FIG. 1, reference numeral 1 indicates a main body of a hair washing apparatus. The washing agent is supplied from the main body 1 through a discharge tube 2. A washing cap 3 is connected to the discharge tube 2. A head is covered with the washing cap 3 in the same manner as a hat so that the entire hair is received within the washing cap 3. A person whose hair is washed sits on a chair in a state in which his head is covered with the washing cap 3, and the backrest of the chair falls backward so that he is almost on his back.

The main body 1 is charged with warm water that is supplied from a cartridge tank 6 and includes the microbubble washing composition that includes the protease and the lipase. Warm water (30 to 40° C.) including the washing composition is discharged from the main body 1 together with microbubbles, and supplied to the washing cap 3 through the discharge tube 2 to wash the braided hair. It is preferable to appropriately adjust the volume and the pressure of water depending on the hairstyle, the hair volume, and the like.

The washing agent is recovered from the washing cap 3 into a filter unit 5 through a recovery tube 4. The filter unit 5 removes hair and dirt (e.g., dandruff) from the washing agent. The washing agent then enters the cartridge tank 6. Since the discharge tube 2 is suspended by a suspension tool S at an appropriate position, the discharge tube 2 and the washing cap 3 do not move downward due to the weight of the washing agent when the washing agent is circulated.

The above apparatus is similar to that disclosed in JP-A-2007-252434.

The washing time is adjusted depending on the type and the concentration of the microbubble washing composition, the hair volume, and the like, but is normally about one minute to several tens of minutes.

The washing temperature is not particularly limited, but is preferably 20 to 40° C. from the viewpoint of achieving excellent washing effects and relaxation.

Since the washing agent including the composition of the present invention and the microbubbles does not adversely affect the cells of a human body, does not damage hair, and is environmentally friendly, the washing agent can be used safely.

Since the washing method of the present invention can safely remove sebum and old keratin adhering to the surface of the pores within a short time, keep the skin clean for a long time, and remove dirt adhering to the surface of hair without untwisting hair, braided hair can be washed conveniently and effectively without collapsing the hairstyle. Since the washing method of the present invention can improve the cleaning effects and reduce the number of washings as compared with a hair washing method using normal shampoo, the hairstyle can be maintained for a long time.

After washing hair, the washing agent is removed by rinsing the washing agent out of the hair with water or warm water, for example. According to the present invention, since almost no bubbles are produced differing from the case of using normal shampoo, the washing agent can be easily removed by merely rinsing the washing agent out of the hair.

The hair is then dried by a normal drying method (e.g., using a drier). A hairstyle almost the same as that before washing can be maintained.

The hair washing effect may be confirmed by the absence of odors and an itch, or may be confirmed by removal of sebum and dandruff adhering to the pores and hair by observing the surface of the skin using a microscope or the like.

EXAMPLES

The present invention is further described below by way of examples. Note that the present invention is not limited to the following examples.

Example 1

Figure 2:
FIG. 2 shows a photograph of hair before washing in Example.
Figure 3:
FIG. 3 shows a photograph of a washing operation in Example.
Figure 4:
FIG. 4 shows a photograph of hair after washing in Example.

The dreadlocks of a woman shown in FIG. 2 were washed using a hair washing apparatus (three shower nozzles were provided instead of the washing cap 3 (refer to the photograph shown in FIG. 3)) similar to that shown in FIG. 1. FIG. 3 shows a photograph of the washing operation, and FIG. 4 shows a photograph of the hair after washing.

A microbubble washing composition including a protease and a lipase had a composition given below. The composition was used in an amount of 5 to 6 g per 5 to 10 liters of warm water. The washing time was 10 minutes, and the temperature of warm water was 39° C.

<Washing Composition>
Borax: 25 wt %, sodium hydrogen carbonate: 25 wt %, sodium sulfate: 50 wt %, pancreatin: 0.1 wt %, Protin AC: 0.15 wt %, lipase: 0.5 wt %, Sylysia: 0.15 wt %, perfume: 0.2 wt %, and dye: 0.12 wt %

Figure 5:
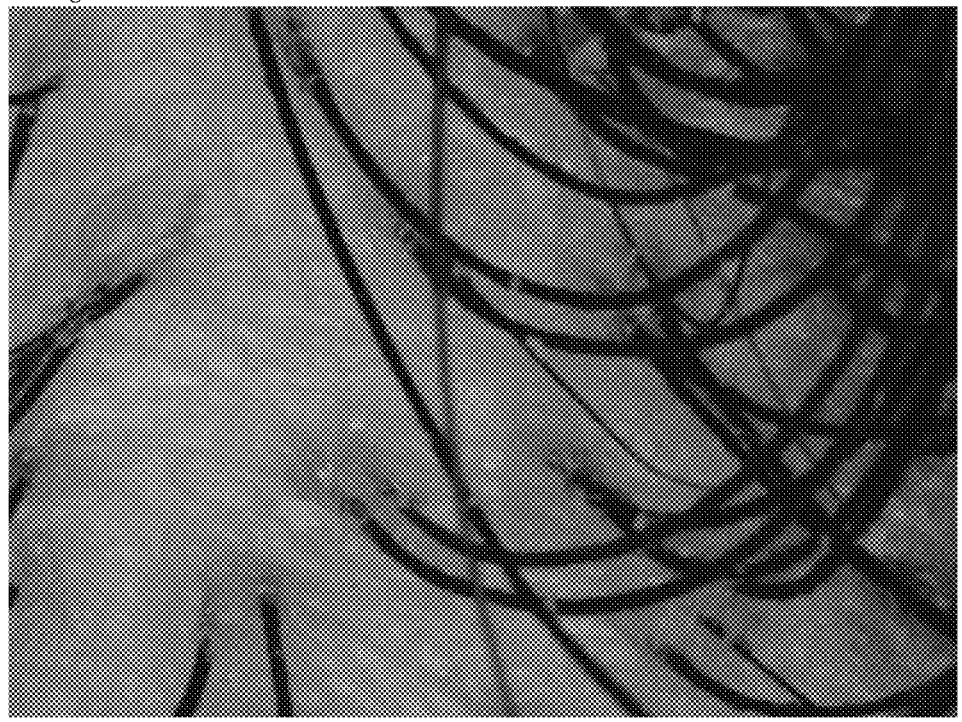
FIG. 5 shows a micrograph of the scalp before washing in Example.
Figure 6:
FIG. 6 shows a micrograph of the scalp after washing in Example.

FIGS. 5 and 6 show micrographs of the scalp before and after washing, respectively. As shown in FIGS. 5 and 6, dandruff adhering to the pores and the hair was removed by washing.

As shown in FIGS. 2 and 4, the hairstyle of the woman changed to only a small extent and was maintained.

Explanation of Symbols

1: main body, 2: discharge tube, 3: washing cap, 4: recovery tube, 5: filter unit, 6: cartridge tank, S: suspension tool

The invention claimed is:

1. A braided hair washing method that washes a person's braided hair without changing a hairstyle, the method comprising washing the person's braided hair using a washing agent that includes a microbubble washing composition, water, and microbubbles, which safely removes dirt, sebum, and old keratin adhering to surfaces of the person's pores and hair without untwisting the braided hair, the microbubble washing composition including at least one alkali metal salt selected from the group consisting of alkali metal carbonates, alkali metal hydrogen carbonates, alkali metal sulfates, alkali metal halides, and alkali metal salts of boron, a protease, and a lipase, and not including a surfactant; removing the washing agent by rinsing the washing agent out of the braided hair with water; and drying the braided hair using a drier such that the hairstyle before washing is maintained.

2. The method according to claim 1, wherein the microbubble washing composition includes the protease in an amount of 0.01 to 0.5 wt % based on the total amount of the microbubble washing composition, and includes the lipase in an amount of 0.1 to 1.0 wt % based on the total amount of the microbubble washing composition.

3. The method according to claim 1, wherein the microbubble washing composition includes the at least one alkali metal salt in an amount of 80 to 99.5 wt % based on the total amount of the microbubble washing composition.

4. The method according to claim 1, wherein the microbubble washing composition is used in an amount of 1 to 10 g per 6 to 10 liters of water.

5. The method according to claim 1, wherein the microbubble washing composition is used in an amount of 1 to 10 g per 6 to 10 liters of water and wherein the microbubble washing composition includes the at least one alkali metal salt in an amount of 80 to 99.5 wt % based on the total amount of the microbubble washing composition.

6. The method according to claim 5, wherein the alkali metal salt is an alkali metal carbonate.

\* \* \* \* \*